United States Patent
Ewart et al.

(10) Patent No.: US 9,440,926 B2
(45) Date of Patent: Sep. 13, 2016

(54) ANTIVIRAL COMPOUNDS AND METHODS

(71) Applicants: Gary Dinneen Ewart, Hackett (AU); Wayne Morris Best, Gosnells (AU)

(72) Inventors: Gary Dinneen Ewart, Hackett (AU); Wayne Morris Best, Gosnells (AU)

(73) Assignee: Biotron Limited, Sydney (AU)

( * ) Notice: Subject to any disclaimer, the term of this patent is extended or adjusted under 35 U.S.C. 154(b) by 0 days.

(21) Appl. No.: 14/071,870

(22) Filed: Nov. 5, 2013

(65) Prior Publication Data

US 2014/0066487 A1 Mar. 6, 2014

Related U.S. Application Data

(62) Division of application No. 11/922,281, filed as application No. PCT/AU2006/000880 on Jun. 23, 2006, now Pat. No. 8,669,280.

(30) Foreign Application Priority Data

Jun. 24, 2005 (AU) .................................. 2005903360

(51) Int. Cl.
| | | |
|---|---|---|
| *A61K 31/415* | (2006.01) | |
| *C07D 231/12* | (2006.01) | |
| *C07D 231/06* | (2006.01) | |
| *C07C 279/22* | (2006.01) | |
| *C07D 213/69* | (2006.01) | |
| *C07D 307/54* | (2006.01) | |
| *C07D 333/22* | (2006.01) | |
| *A61K 45/06* | (2006.01) | |

(52) U.S. Cl.
CPC .......... *C07D 231/06* (2013.01); *A61K 31/415* (2013.01); *A61K 45/06* (2013.01); *C07C 279/22* (2013.01); *C07D 213/69* (2013.01); *C07D 231/12* (2013.01); *C07D 307/54* (2013.01); *C07D 333/22* (2013.01)

(58) Field of Classification Search
CPC ........................... C07D 231/12; A61K 31/415
USPC ........................... 514/406; 548/377.1, 373.1
See application file for complete search history.

(56) References Cited

U.S. PATENT DOCUMENTS

| | | |
|---|---|---|
| 2,734,904 A | 2/1956 | Burtner |
| 4,251,545 A | 2/1981 | Resnick |
| 5,292,755 A | 3/1994 | Englert et al. |
| 6,025,349 A | 2/2000 | Schwark et al. |
| 6,087,304 A | 7/2000 | Brendel et al. |
| 2001/0020042 A1 | 9/2001 | Schwark et al. |
| 2003/0113352 A1 | 6/2003 | Elias et al. |

(Continued)

FOREIGN PATENT DOCUMENTS

| | | |
|---|---|---|
| DE | 4421536 A1 | 12/1995 |
| EP | 0744397 A2 | 11/1996 |

(Continued)

OTHER PUBLICATIONS

U.S. Appl. No. 14/615,616, filed Feb. 6, 2015.

(Continued)

*Primary Examiner* — Shengjun Wang
(74) *Attorney, Agent, or Firm* — Amster, Rothstein & Ebenstein LLP

(57) ABSTRACT

The present invention relates to novel compounds and compositions having antiviral activity. The invention also relates to methods for the therapeutic or prophylactic treatment of viral infections in mammals.

14 Claims, 2 Drawing Sheets

(56) References Cited

U.S. PATENT DOCUMENTS

2007/0099968 A1    5/2007   Gage et al.
2013/0035328 A1    2/2013   Gage et al.

FOREIGN PATENT DOCUMENTS

| | | |
|---|---|---|
| EP | 0810206 A1 | 12/1997 |
| JP | 3106858 A | 5/1991 |
| JP | 8027093 A | 1/1996 |
| JP | 08225513 A | 9/1996 |
| JP | 08511243 A | 11/1996 |
| JP | 8319266 A | 12/1996 |
| JP | 10081664 A | 3/1998 |
| JP | 10316647 A | 12/1998 |
| JP | 2000506515 A | 5/2000 |
| JP | 218632 | 3/2012 |
| WO | 9426709 | 11/1994 |
| WO | 2004056181 A1 | 7/2004 |
| WO | 2004112687 A2 | 12/2004 |

OTHER PUBLICATIONS

Yamamoto et al. "Structural Requirements for Potent Na/H Exchange Inhibitors Obtained from Quantitative Structure-Activity Relationships of Monocyclic and Bicyclic Aroylguanidines." Chem. Pharm. Bull. 45(8), 1997, pp. 1282-1286.

Yamamoto et al. STN File CA Abstract Accession No. 127:257127, Chemical and Pharmaceutical Bulletin 1997, vol. 45:8, pp. 1282-1286.

Bream et al. "Substituted Phenylucetylguanidines: a New Class of Antihypertensive Agents." Laboratories of the Research Institute Wander (Switzerland and Kings Langley, Herts, England), Arzneimittel-Forschung, 1975, vol. 25, No. 10, pp. 1477-1482.

Bream et al. STN File CA Abstract Accession No. 84:12322, Arzneimittel-Forchung 1975, vol. 25:10, pp. 1477-1482.

IN 177137, Naik et al. 1996, CAPLUS Abstract, Document No. 140:27667.

CAS Registration No. 633297-24-2, 2004.

Office Action for related Japanese Application No. 2008-517277 dated Mar. 29, 2012.

Office Action for Chinese Application No. 200680022641.0, dated Mar. 1, 2010.

International Search Report of the International Searching Authority for PCT Application No. PCT/AU2006/000880, dated Aug. 16, 2006.

International Preliminary Report on Patentability for PCT Application No. PCT/AU2006/000880, dated May 28, 2007.

ANTIVIRAL COMPOUNDS AND METHODS

CROSS-REFERENCE TO RELATED APPLICATIONS

This is a divisional of U.S. application Ser. No. 11/992,281, filed Dec. 14, 2007, which is a U.S. national phase of PCT Application No. PCT/AU2006/000880, filed Jun. 23, 2006, which claims priority to Australian Application No. 2005903360, filed Jun. 24, 2005, the contents each of which is hereby incorporated by reference.

FIELD OF INVENTION

The present invention relates to novel compounds and compositions having antiviral activity. The invention also relates to methods for retarding, reducing or otherwise inhibiting viral growth and/or functional activity.

BACKGROUND OF THE INVENTION

Currently, there is a great need for the development of new treatments that are effective against viral infections, particularly against viral infections which are associated with high morbidity and mortality, and which impact on sizable populations. Treatments currently available are inadequate or ineffective in large proportions of infected patients.

A large number of viruses contribute to the pool of significant human pathogens. Examples of these include the viruses of the Lentivirus and Flavivirus families, for example HIV, Hepatitis C virus (HCV), Dengue virus and the like.

To improve the prospect of treating and preventing viral infections, and to deal with ongoing viral evolution, there is an on-going need to identify molecules capable of inhibiting various aspects of the viral life cycle. A number of such compounds is disclosed in PCT/AU2004/000866. However, there is still a need for additional novel compositions and agents with antiviral activity.

It is an object of the present invention to overcome or ameliorate at least one of the disadvantages of the prior art, or to provide a useful alternative.

Any discussion of the prior art throughout the specification should in no way be considered as an admission that such prior art is widely known or forms part of common general knowledge in the field.

SUMMARY OF THE INVENTION

The inventors have surprisingly found that certain compounds that fall under the classification of substituted acylguanidines have antiviral activity against viruses from a range of different virus families. A number of such compounds is disclosed in PCT/AU2004/000866, incorporated in its entirety herein by reference.

The present invention is concerned with certain novel antiviral compounds that fall under the classification of substituted acylguanidines.

According to a first aspect, the present invention provides compound of Formula I:

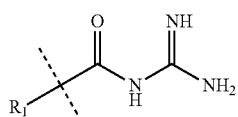
(I)

wherein

R1 is phenyl, substituted phenyl, naphthyl, substituted naphthyl or R1 is selected from

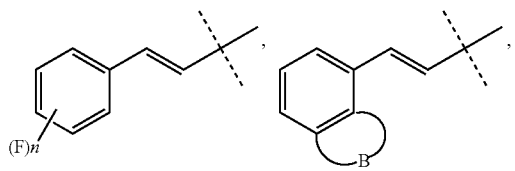

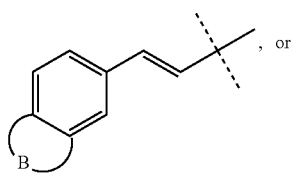

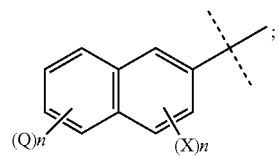

and n is 1, 2, 3 or 4;

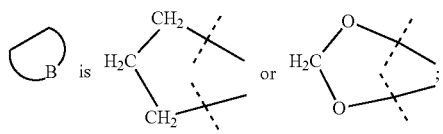

F is independently

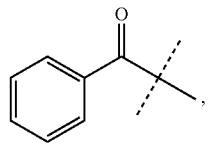

halogen, alkyl, halo or polyhalo alkyl;

Q is independently hydrogen, alkoxy especially methoxy, alkyl especially methyl, cycloalkyl, thienyl, furyl, pyrazolyl, substituted pyrazolyl, pyridyl, substituted pyridyl, phenyl, substituted phenyl, halo especially chloro or bromo, heterocycle ("het"), or Q is independently selected from

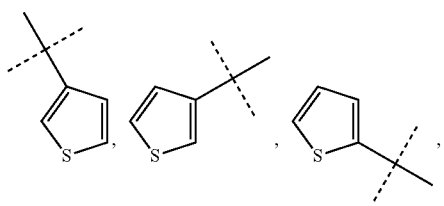

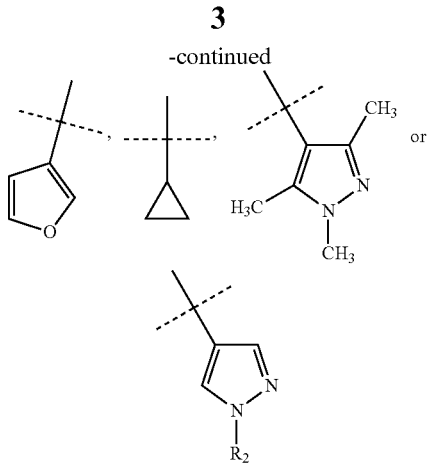

wherein R2 is straight or branched chain alkyl,

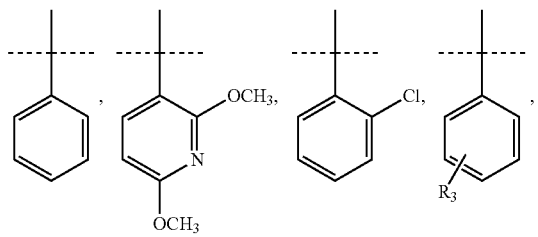

where R3 is

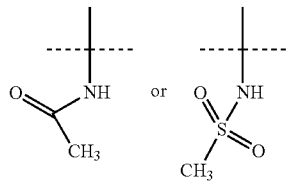

and

X is hydrogen or alkoxy, and pharmaceutically acceptable salts thereof.

To the extent that any of the compounds were previously described in PCT/AU2004/000866 as anti-viral agents they are excluded from the present invention.

Preferably, the compounds of the invention include the following:
(3-benzoyl)cinnamoylguanidine,
5-methyl-2-napthoylguanidine,
3(indan-4-yl)-propenoylguanidine,
5-bromo-6-methoxy-2-napthoylguanidine,
5-thiophen-3-yl-2-naphthoylguanidine,
5-(1-methylpyrazol-4-yl)2-naphthoylguanidine,
2,3-methylenedioxycinnamoyl guanidine,
(1-methoxy-2-napthoyl)guanidine,
(3-methoxy-2-napthoyl)guanidine,
(5-bromo-2-napthoyl)guanidine,
(1,4-dimethoxy-2-napthoyl)guanidine,
(6-(3-thienyl)-2-napthoyl)guanidine,
(6-methyl-2-napthoyl)guanidine,
(5-phenyl-2-napthoyl)guanidine,
(5-(thien-2-yl)-2-napthoyl)guanidine,
(5-(1,3,5-trimethylpyrazol-4-yl)-2-napthoyl)guanidine,
(5-(1-isobutyl-1H-pyrazol-4-yl)-2-napthoyl)guanidine,
(5-(3-furyl)-2-napthoyl)guanidine,
(5-cyclopropyl-2-napthoyl)guanidine,
(5-chloro-2-napthoyl)guanidine,
(6-(1-methylpryazol-4-yl)-2-napthoyl)guanidinium acetate,
(5-(2,6-dimethoxypyridin-3-yl)-2-napthoyl)guanidine,
(5-(2-chlorophenyl)-2-napthoyl)guanidine,
(5-(4-(acetylamino)phenyl)-2-napthoyl)guanidine,
(5-(3-(acetylamino)phenyl)-2-napthoyl)guanidine,
(5-(4-((methylsulphonyl)amino)phenyl)-2-napthoyl)guanidine, and pharmaceutically acceptable salts thereof.

The amine or imine groups of the guanidyl portion of the compounds of Formula I can be present in any conventional form used for the provision of such compounds. For example, they may be present as the free base, a hydrate, an organic or inorganic salt or combinations thereof.

Preferably, the compounds of the invention possess antiviral activity and are capable of reducing, retarding or otherwise inhibiting viral growth and/or replication. Examples of preferred viruses against which the compounds of the present invention are active, are viruses from the Lentivirus and Flavivirus families. More preferably, the virus is Hepatitis C virus (HCV), Human Immunodeficiency Virus (HIV) or Dengue virus. Most preferably, the virus is HCV, HIV-1 and HIV-2.

According to a second aspect, the present invention provides a pharmaceutical composition comprising a compound according to the first aspect, and optionally one or more pharmaceutical acceptable carriers or derivatives. The active compounds may be present in the form of any suitable salt, adduct, in anhydrous or solvated forms.

In one embodiment, the compositions of the invention further comprise one or more known compounds or molecules having antiviral activity. The known antiviral compounds can be selected from the group consisting of Vidarabine, Acyclovir, Ganciclovir, Valganciclovir, Valacyclovir, Cidofovir, Famciclovir, Ribavirin, Amantadine, Rimantadine, Interferon, Oseltamivir, Palivizumab, Rimantadine, Zanamivir, nucleoside-analog reverse transcriptase inhibitors (NRTI) such as Zidovudine, Didanosine, Zalcitabine, Stavudine, Lamivudine and Abacavir, non-nucleoside reverse transcriptase inhibitors (NNRTI) such as Nevirapine, Delavirdine and Efavirenz, protease inhibitors such as Saquinavir, Ritonavir, Indinavir, Nelfinavir, Amprenavir, and other known antiviral compounds and preparations.

According to a third aspect, there is provided a method for reducing, retarding or otherwise inhibiting growth and/or replication of a virus comprising contacting a cell infected with said virus or exposed to said virus with a compound according to the first aspect.

According to a fourth aspect, there is provided a method for preventing the infection of a cell exposed to a virus comprising contacting said cell with a compound according to the first aspect.

According to a fifth aspect of the invention, there is provided a method for the therapeutic or prophylactic treatment of a subject exposed to or infected with a virus comprising the administration to said subject of a compound according to the first aspect.

Preferably, the virus is from the Lentivirus and Flavivirus families. More preferably, the virus is Hepatitis C virus (HCV), Human Immunodeficiency Virus (HIV) or Dengue virus. Most preferably, the virus is HCV, HIV-1 and HIV-2.

Preferably, the subject undergoing therapeutic or prophylactic treatment is a mammal, such as, but not limited to, a human, primate, livestock animal (e.g. sheep, cow, horse, donkey, pig), companion animal (e.g. dog, cat), laboratory test animal (e.g. mouse, rabbit, rat, guinea pig, hamster), or captive wild animal (e.g. fox, deer). Preferably, the subject is a primate. Most preferably, the subject is a human.

Preferably, the pharmaceutical composition may further comprise one or more known antiviral compounds or molecules. The known antiviral compounds can be selected from the group consisting of Vidarabine, Acyclovir, Ganciclovir, Valganciclovir, Valacyclovir, Cidofovir, Famciclovir, Ribavirin, Amantadine, Rimantadine, Interferon, Oseltamivir, Palivizumab, Rimantadine, Zanamivir, nucleoside-analog reverse transcriptase inhibitors (NRTI) such as Zidovudine, Didanosine, Zalcitabine, Stavudine, Lamivudine and Abacavir, non-nucleoside reverse transcriptase inhibitors (NNRTI) such as Nevirapine. Delavirdine and Efavirenz, protease inhibitors such as Saquinavir, Ritonavir, Indinavir, Nelfinavir, Amprenavir, and other known antiviral compounds and preparations.

In the event of any inconsistencies in the present specification between the named compounds and the structural formula, the structural formula is to be preferred.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

DETAILED DESCRIPTION OF THE INVENTION

Figure 1:
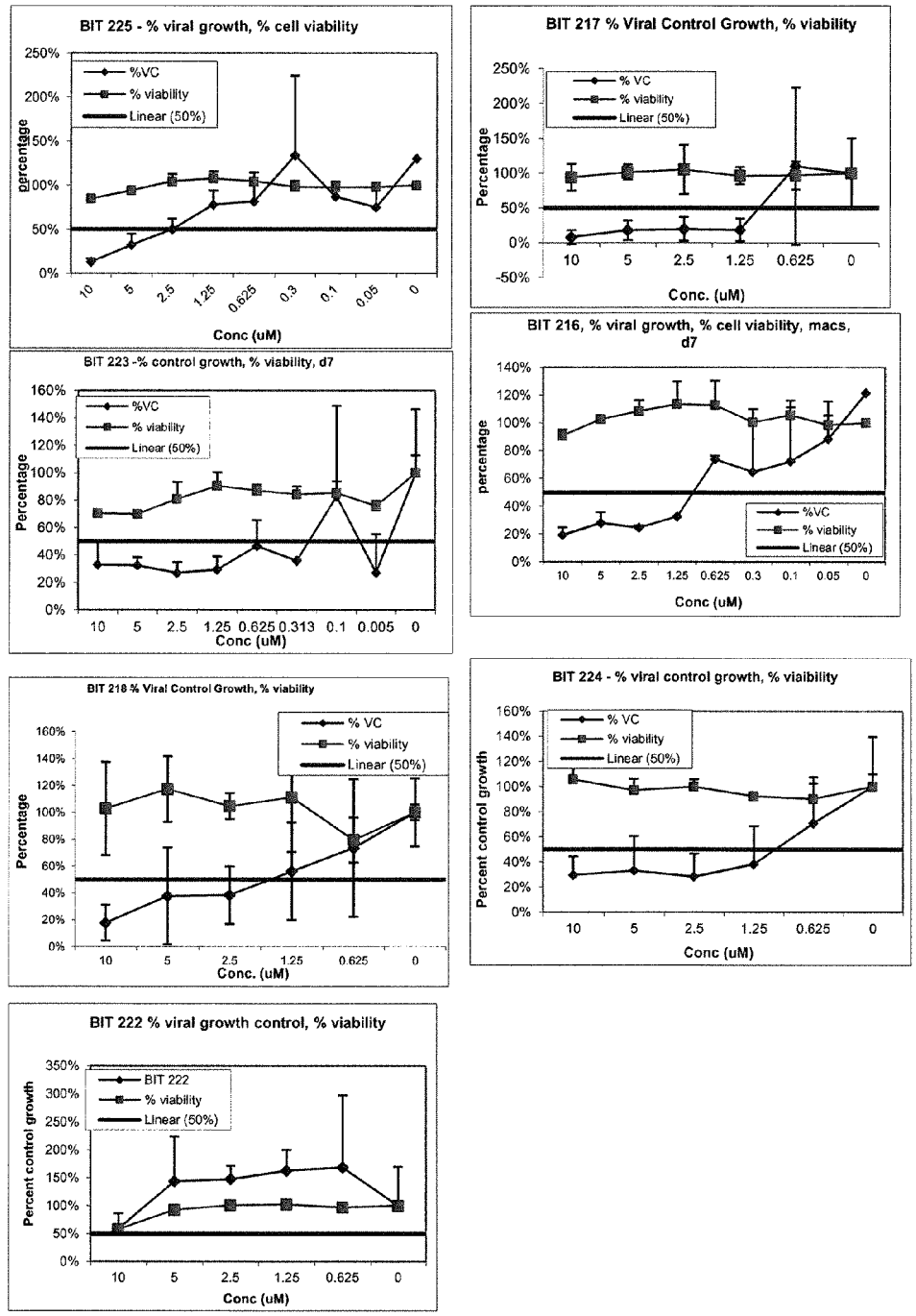
FIG. 1, BIT compound HIV-1$_{Ba-L}$ inhibition and cell cytotoxicity in primary human macrophages. The "% VC" dose response curves represent "percentage of control virus growth" figures calculated based on mean (of triplicate wells) virus levels in wells containing compound (at decreasing conc.) compared to controls (no compound). HIV-1 levels were determined using p24 ELISA and converted to the percentage of control values based on virus p24 levels detected in control culture wells that did not contain compound. The "% viability" curve was calculated from OD560 nm data generated from MTT assays as a measure of cell viability. The OD values (mean of triplicate wells) were converted to a percentage of controls (containing no compound). The 50% level is indicated by the horizontal line to allow for estimation of IC$_{50}$ and TC$_{50}$ values.

The present invention is based, in part, on the surprising observation that certain substituted acylguanidines have antiviral activity against a broad range of viruses including those of the Lentivirus and Flavivirus families.

The present invention concerns compound of Formula I:

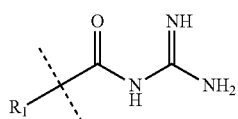
(I)

wherein
R1 is phenyl, substituted phenyl, naphthyl, substituted naphthyl or R1 is selected from

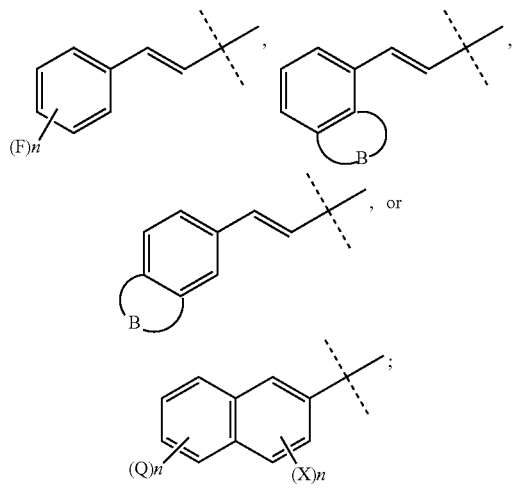

and
n is 1, 2, 3 or 4;

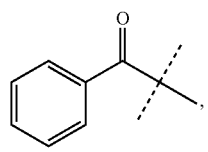

F is independently

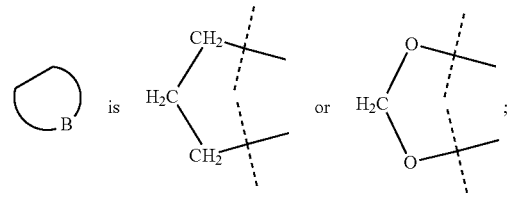

halogen, alkyl, halo or polyhalo alkyl;
Q is independently hydrogen, alkoxy especially methoxy, alkyl especially methyl, cycloalkyl, thienyl, furyl, pyrazolyl, substituted pyrazolyl, pyridyl, substituted pyridyl, phenyl, substituted phenyl, halo especially chloro or bromo, heterocycle ("het"), or Q is independently selected from

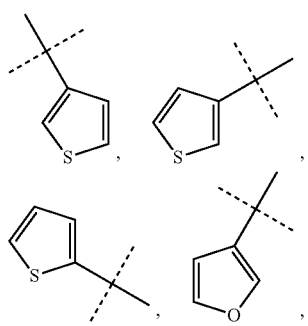

-continued

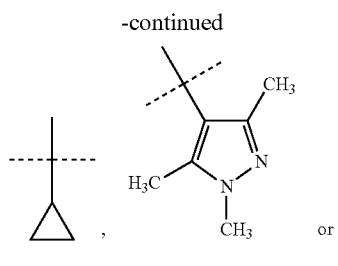
or

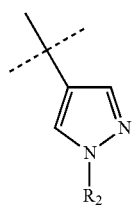

wherein R2 is straight or branched chain alkyl,

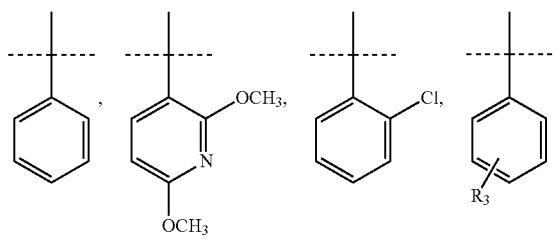

where R3 is

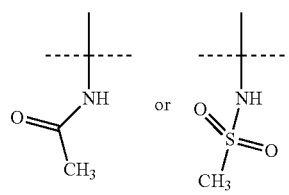

and

X is hydrogen or alkoxy, and pharmaceutically acceptable salts thereof.

To the extent that any of the compounds have been described previously in PCT/AU2004/000866 as anti-viral agents, they are excluded from the present invention. Particularly useful compounds may be selected from the following:

(3-benzoyl)cinnamoylguanidine comprising the structure

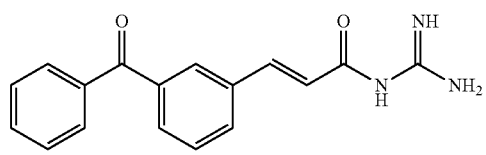

BIT-216

2,3-methylenedioxycinnamoyl guanidine comprising the structure

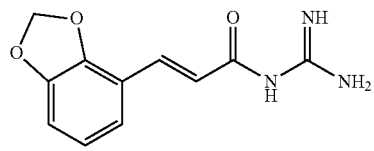

BIT-217

5-methyl-2-napthoylguanidine comprising the structure

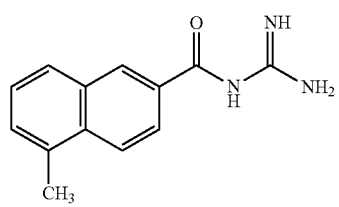

BIT-218

3(indan-4-yl)-propenoylguanidine comprising the structure

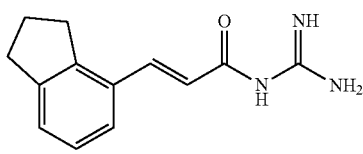

BIT-222

5-bromo-6-methoxy-2-napthoylguanidine comprising the structure

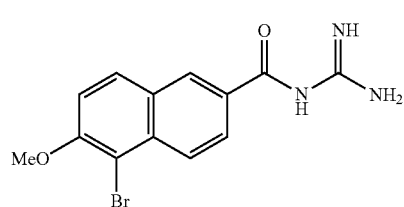

BIT-223

5-thiophen-3-yl-2-naphthoylguanidine comprising the structure

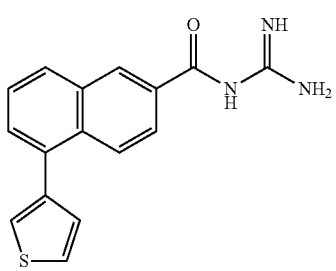

BIT-224

5-(1-methylpyrazol-4-yl)2-naphthoylguanidine comprising the structure

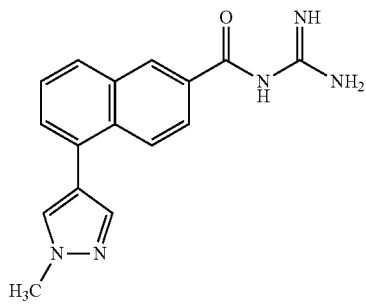
BIT-225

(1-methoxy-2-napthoyl)guanidine comprising the structure

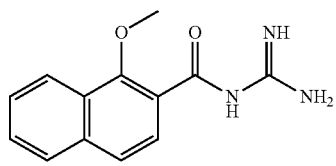
BIT-301

(3 methoxy-2-napthoyl)guanidine comprising the structure

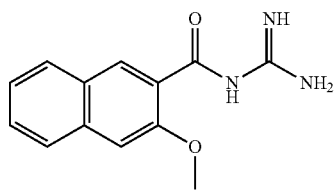
BIT-302

(5-bromo-2-napthoyl)guanidine comprising the structure

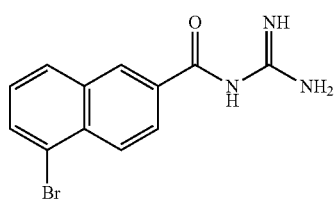
BIT-303

(1,4-dimethoxy-2-napthoyl)guanidine comprising the structure

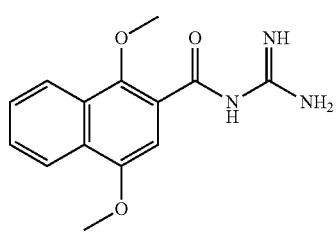
BIT-304

(6-(3-thienyl)-2-napthoyl)guanidine comprising the structure

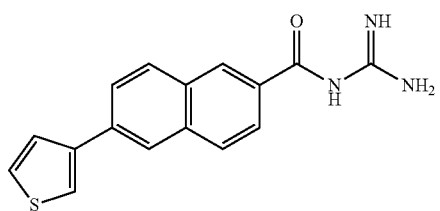
BIT-305

(6-methyl-2-napthoyl)guanidine comprising the structure

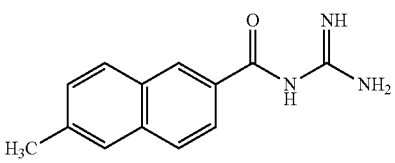
BIT-306

(5-phenyl-2-napthoyl)guanidine comprising the structure

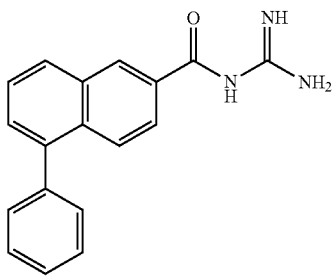
BIT-307

(5-(thien-2-yl)-2-napthoyl)guanidine comprising the structure

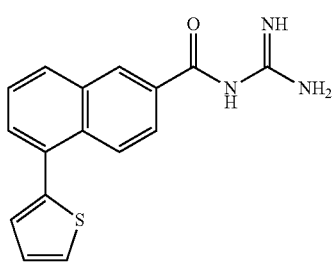
BIT-308

(5-(1,3,5-trimethylpyrazol-4-yl)-2-napthoyl)guanidine comprising the structure

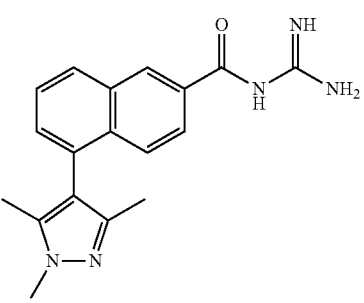
BIT-309

(5-(1-isobutyl-1H-pyrazol-4-yl)-2-napthoyl)guanidine comprising the structure

BIT-310

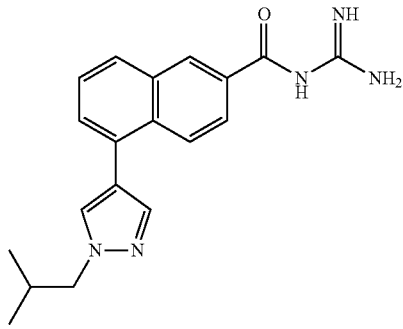

(5-(3-furyl)-2-napthoyl)guanidine comprising the structure

BIT-311

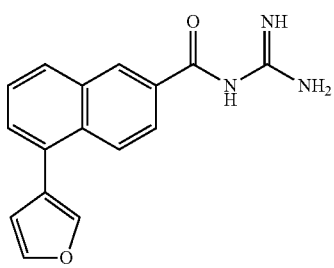

(5-cyclopropyl-2-napthoyl)guanidine

BIT-312

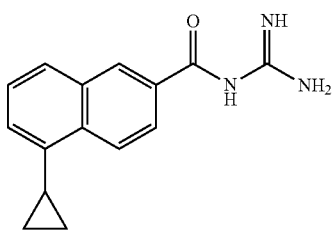

(5-chloro-2-napthoyl)guanidine

BIT-313

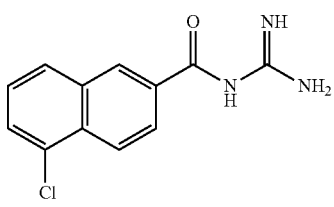

(6-(1-methylpryazol-4-yl)-2-napthoyl)guanidinium acetate

BIT-314

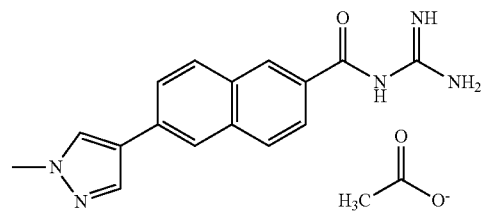

(5-(2,6-dimethoxypyridin-3-yl)-2-napthoyl)guanidine,

BIT-315

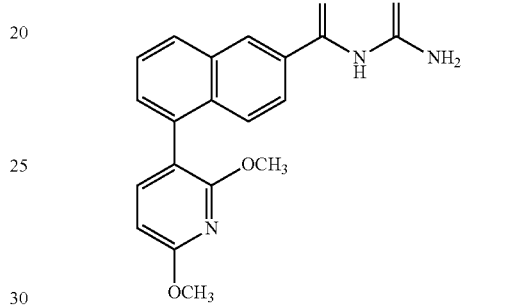

(5-(2-chlorophenyl)-2-napthoyl)guanidine

BIT-316

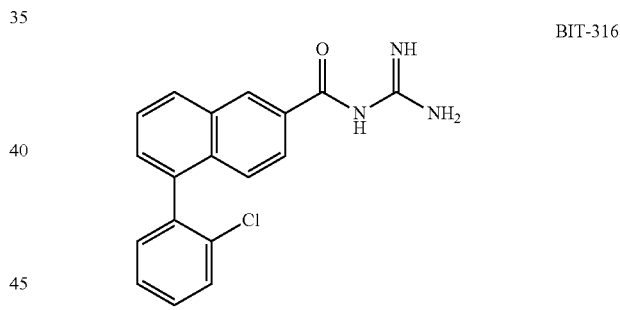

(5-(4-(acetylamino)phenyl)-2-napthoyl)guanidine

BIT-317

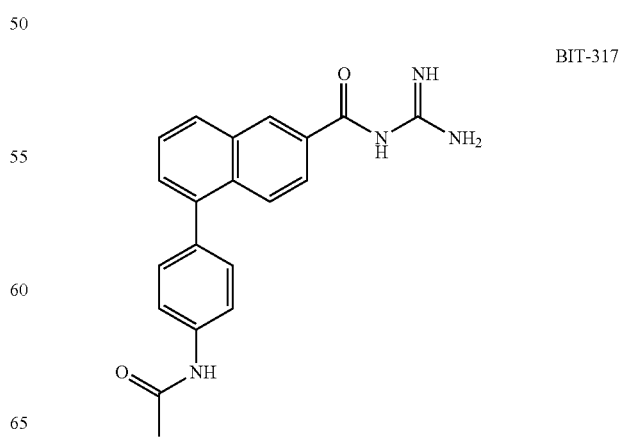

(5-(3-(acetylamino)phenyl)-2-napthoyl)guanidine

BIT-318

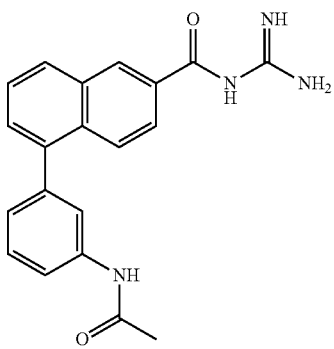

(5-(4-((methylsulphonyl)amino)phenyl)-2-napthoyl)guanidine

BIT-319

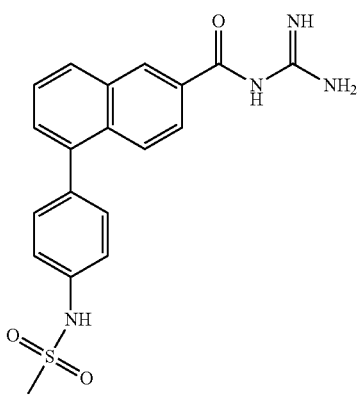

and pharmaceutically acceptable salts thereof. The amine or imine groups of the guanidyl portion of the compounds of Formula I can be present in any conventional form used for the provision of such compounds. For example, they maybe present as the free base, a hydrate, an organic or inorganic salt or combinations thereof.

The methods developed for screening the compounds of the present invention for antiviral activity are described in detail in PCT/AU2004/000866, incorporated in its entirety herein by reference.

Reference to "HIV", "HCV" and "Dengue virus" and the like should be understood as a reference to any HIV, HCV or Dengue virus strain and including homologues and mutants.

Reference to the "functional activity" of a virus should be understood as a reference to any one or more of the functions which a virus performs or is involved in.

Reference to the "viral replication" should be understood to include any one or more stages or aspects of the viral life cycle, such as inhibiting the assembly or release of virions. Accordingly, the method of the present invention encompasses the mediation of viral replication via the induction of a cascade of steps which lead to the mediation of any one or more aspects or stages of the viral life cycle.

Reference to a "cell" infected with a virus should be understood as a reference to any cell, prokaryotic or eukaryotic, which has been infected with a virus. This includes, for example, immortal or primary cell lines, bacterial cultures and cells in situ.

It will be understood by those skilled in the art that the compounds of the invention may be administered in the form of a composition or formulation comprising pharmaceutically acceptable carriers and/or excipients.

The pharmaceutical compositions of the invention may further comprise one or more known antiviral compounds or molecules. Preferably, the known antiviral compounds are selected from the group consisting of Vidarabine, Acyclovir, Ganciclovir, Valganciclovir, Valacyclovir, Cidofovir, Famciclovir, Ribavirin, Amantadine, Rimantadine, Interferon, Oseltamivir, Palivizumab, Rimantadine, Zanamivir, nucleoside-analog reverse transcriptase inhibitors (NRTI) such as Zidovudine, Didanosine, Zalcitabine, Stavudine, Lamivudine and Abacavir, non-nucleoside reverse transcriptase inhibitors (NNRTI) such as Nevirapine, Delavirdine and Efavirenz, protease inhibitors such as Saquinavir, Ritonavir, Indinavir, Nelfinavir, Amprenavir, and other known antiviral compounds and preparations.

The subject of the viral inhibition is a mammal, such as, but not limited to a human, primate, livestock animal (e.g. sheep, cow, horse, donkey, pig), companion animal (e.g. dog, cat), laboratory test animal (e.g. mouse, rabbit, rat, guinea pig, hamster), or captive wild animal (e.g. fox, deer). Preferably, the subject is a human. Most preferably, the subject is a human.

The method of the present invention is useful in the treatment and prophylaxis of viral infection such as, for example, HIV, HCV, Dengue and other viral infections. For example, the antiviral activity may be affected in subjects known to be infected with HIV in order to prevent replication of HIV thereby preventing the onset of AIDS. Alternatively, the method of the present invention may be used to reduce serum viral load or to alleviate viral infection symptoms. This concept applies to any viral infection.

The method of the present invention may be particularly useful either in the early stages of viral infection to prevent the establishment of a viral reservoir in affected cells or as a prophylactic treatment to be applied immediately prior to or for a period after exposure to a possible source of virus.

Reference herein to "therapeutic" and "prophylactic" is to be considered in their broadest contexts. The term "therapeutic" does not necessarily imply that a mammal is treated until total recovery. Similarly, "prophylactic" does not necessarily mean that the subject will not eventually contract a disease condition. Accordingly, therapy and prophylaxis include amelioration of the symptoms of a particular condition or preventing or otherwise reducing the risk of developing a particular condition. The term "prophylaxis" may be considered as reducing the severity of onset of a particular condition. Therapy may also reduce the severity of an existing condition or the frequency of acute attacks.

In accordance with the methods of the present invention, more than one compound or composition may be co-administered with one or more other compounds, such as known anti-viral compounds or molecules. By "co-administered" is meant simultaneous administration in the same formulation or in two different formulations via the same or different routes or sequential administration by the same or different routes. By "sequential" administration is meant a time difference of from seconds, minutes, hours or days between the administration of the two or more separate compounds. The subject antiviral compounds may be administered in any order.

Routes of administration include, but are not limited to, intravenous, intraperitoneal, subcutaneous, intracranial, intradermal, intramuscular, intraocular, intrathecal, intracerebral, intranasal, transmucosal, or by infusion orally, rectally, via iv drip, patch and implant. Intravenous routes are particularly preferred.

Compositions suitable for injectable use include sterile aqueous solutions (where water soluble) and sterile powders for the extemporaneous preparation of sterile injectable solutions. The carrier can be a solvent or dispersion medium containing, for example, water, ethanol, polyol (for example, glycerol, propylene glycol and liquid polyethylene glycol, and the like), suitable mixtures thereof and vegetable oils. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by, for example, filter sterilization or sterilization by other appropriate means. Dispersions are also contemplated and these may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

When the active ingredients are suitably protected, they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.01% by weight, more preferably 0.1% by weight, even more preferably 1% by weight of active compound. The percentage of the compositions and preparations may, of course, be varied and may conveniently be between about 1 to about 99%, more preferably about 2 to about 90%, even more preferably about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 ng and 2000 mg of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels. In such forms, the anti-clotting peptides may need to be modified to permit penetration of the surface barrier.

Procedures for the preparation of dosage unit forms and topical preparations are readily available to those skilled in the art from texts such as *Pharmaceutical Handbook. A Martindale Companion Volume* Ed. Ainley Wade Nineteenth Edition The Pharmaceutical Press London, *CRC Handbook of Chemistry and Physics* Ed. Robert C. Weast Ph D. CRC Press Inc.; *Goodman and Gilman's; The Pharmacological basis of Therapeutics*. Ninth Ed. McGraw Hill; *Remington; and The Science and Practice of Pharmacy*. Nineteenth Ed. Ed. Alfonso R. Gennaro Mack Publishing Co. Easton Pa.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding.

Effective amounts contemplated by the present invention will vary depending on the severity of the condition and the health and age of the recipient. In general terms, effective amounts may vary from 0.01 ng/kg body weight to about 100 mg/kg body weight.

Alternative amounts include for about 0.1 ng/kg body weight about 100 mg/kg body weight or from 1.0 ng/kg body weight to about 80 mg/kg body weight.

The subject of the viral inhibition is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably, the subject is a human or primate. Most preferably, the subject is a human.

The present invention will now be described in more detail with reference to specific but non-limiting examples describing synthetic protocols, viral inhibition and other anti-viral properties of the compounds of the present invention. Synthesis and screening for compounds that have antiviral activity can be achieved by the range of methodologies described herein or described in more detail in PCT/AU2004/000866, incorporated in its entirety herein by reference.

It is to be understood, however, that the detailed description of specific procedures, compounds and methods is included solely for the purpose of exemplifying the present invention. It should not be understood in any way as a restriction on the broad description of the invention as set out above.

EXAMPLES

Anti-viral activity of all the compounds of the present invention can be, and has been, ascertained using the methods described herein or described in detail in PCT/AU2004/000866, incorporated in its entirety herein by reference. Further, methods for synthesis of the compounds of the invention, both generic and specific, described herein, described in referenced publications or otherwise known to those skilled in the art, can be used to prepare all the compounds of the present invention.

More specifically, acylguanidines can be synthesised by a variety of methods including reacting guanidine (generally generated in situ from its hydrochloride salt) with a suitably activated derivative of a carboxylic acid. Examples include:
i) synthesis from acid chlorides, exemplified by Yamamoto et al., *Chem. Pharm. Bull.*, 1997, 45, 1282
ii) synthesis from simple esters, exemplified by U.S. Pat. No. 2,734,904,
iii) synthesis from carboxylic acids, via in situ activation by carbonyldiimidazole, exemplified by U.S. Pat. No. 5,883, 133

The carboxylic acid precursors required for the preparation of the acylguanidines described herein were obtained by a variety of diverse methods. A large number of the substituted cinnamic acids are commercially available. In addition, numerous procedures for the synthesis of substituted cinnamic acids and their simple esters are well described in the art, including:
i) The reaction of malonic acid with an aromatic aldehyde and base (the Doebner Condensation), described in *Chemical Reviews*, 1944, 35, 156, and references contained therein,
ii) The reaction of acetic anhydride with an aromatic aldehyde and base (the Perkin Reaction), described in *Organic Reactions*, 1942, 1, 210, and references contained therein.
iii) The reaction of acrylic acid and simple esters thereof with an aromatic halide or aromatic triflate using palladium catalyst (the Heck Reaction), described in *Organic Reactions*, 1982, 28, 345, and references contained therein.
iv) The reaction of a trialkyl phosphonoacetate with an aromatic aldehyde and base (the Horner-Emmons Reaction), described in *Organic Reactions*, 1977, 25, 73, and references contained therein.

A number of simple halo, hydroxy, and alkoxy substituted naphthoic acids are either commercially available or known in the art and these provided the starting materials for the substituted naphthoylguanidines.

Naphthoic acids which are substituted with alkyl, cycloalkyl, aryl, and heterocyclic groups can often be prepared by reacting a halonaphthoic acid with a suitable organometallic reagent using a transition metal catalyst. One such variant of this methodology which was used to prepare a number of the substituted naphthoic acids used as precursors to the naphthoylguanidines described herein, was the palladium-catalyzed carbon-carbon bond forming reaction between bromonaphthoic acids and a suitably substituted boronic acid (or boronate ester) which is widely known in the art as the Suzuki coupling (described in *Chemical Reviews*, 1995, 95, 2457 and references therein). The reaction has wide applicability and can be used on a range of substituted halonaphthalenes which can then be further elaborated to introduce or unmask the required carboxylic acid group.

1. General Synthetic Methodology 1.1 General Procedure A—Preparation of Aryl Triflates To a solution of the phenol (10 mmol) in pyridine (7 mL) at 0° C. was slowly added trifluoromethanesulphonic anhydride (11 mmol, 1.1 eq). The resulting mixture was stirred at 0° C. for a further 5 minutes before being allowed to warm to room temperature and stirred until TLC analysis showed that the starting phenol had been consumed. The mixture was then poured into water and extracted with ethyl acetate (×3). The combined extracts were washed sequentially with water, 1M aqueous hydrochloric acid, water and brine, then dried ($MgSO_4$) and concentrated in vacuo to give the crude product. The crude products were chromatographed over silica gel. Elution with a mixture of ethyl acetate/hexanes gave the desired aryl triflates, generally as colourless oils.

1.2 General Procedure B—Cinnamate Esters Via Heck Reaction of Triflates

A mixture of the phenyl triflate (10 mmol), methyl acrylate (14 mmol, 1.4 eq), triethylamine (40 mmol, 4 eq) and dichlorobis(triphenylphosphine)palladium (0.3 mmol, 0.03 eq) in dimethylformamide (30 mL) was heated at 90° C. The reaction was monitored by GC/MS and fresh batches of methyl acrylate (1 eq), triethylamine (2 eq) and the palladium catalyst (0.03 eq) were added as required, in an effort to force the reaction to completion. The mixture was then poured into water and extracted with a 1:1 mixture of diethyl ether/hexanes (×3). The combined extracts were washed with water, then brine, dried ($MgSO_4$), filtered through a pad of silica gel and the filtrate was concentrated in vacuo to give the crude product as an oil. The crude products were chromatographed over silica gel. Elution with a mixture of ethyl acetate/hexanes gave the desired methyl cinnamates, generally as colourless oils.

1.3 General Procedure C—Cinnamate Esters Via Heck Reaction of Bromides

The aryl bromide (10 mmol), palladium acetate (0.1 mmol, 0.01 eq) and tri-o-tolylphosphine (0.4 mmol, 0.04 eq) was added to the reaction flask and purged with nitrogen. To this, methyl acrylate (12.5 mmol, 1.25 eq), triethylamine (12.5 mmol, 1.25 eq) and dimethylformamide (1 mL) were then added and the mixture was heated at 100° C. The reaction was monitored by GC/MS and fresh batches of palladium acetate (0.01 eq), tri-o-tolylphosphine (0.04 eq), methyl acrylate (1.25 eq) and triethylamine (1.25 eq) were added as required, in an effort to force the reaction to completion. The mixture was poured into water and extracted with a 1:1 mixture of diethyl ether/hexanes (×4). The combined extracts were washed with water, then brine, dried ($MgSO_4$), filtered through a pad of silica gel and the filtrate was concentrated in vacuo to give the crude product. The crude products were chromatographed over silica gel. Elution with a mixture of ethyl acetate/hexanes gave the desired methyl cinnamates, generally as colourless oils.

1.4 General Procedure D—Cinnamate Esters Via Horner-Emmons Reaction

A solution of triethyl phosphonoacetate (13 mmol, 1.3 eq) in anhydrous tetrahydrofuran (10 mL) was added, over 5 minutes, to a suspension of sodium hydride (14.3 mmol, 1.4 eq) in anhydrous tetrahydrofuran (10 mL) at 0° C. under nitrogen. The mixture was then stirred at 0° C. for 20 minutes. A solution of the benzaldehyde (0 mmol) in tetrahydrofuran (15 mL) was then added over 10 minutes at 0° C. The mixture was stirred at 0° C. for a further 30 minutes before being allowed to stir at room temperature until GC/MS or TLC analysis showed that the benzaldehyde starting material had been consumed. Typically, reactions were allowed to stir at room temperature overnight to ensure complete consumption of the starting aldehyde. The mixture was poured into water, the organic layer was separated and the aqueous layer was extracted with ethyl acetate (×3). The combined organic extracts were then washed with water, then brine, dried (MgSO4) and concentrated in vacuo to give the crude product. The crude products were chromatographed over silica gel. Elution with a mixture of ethyl acetate/hexanes gave the desired ethyl cinnamates, generally as colourless oils.

1.5 General Procedure E—Preparation of 5-Phenylpenta-2,4-Dienoic Esters

A solution of triethyl 4-phosphonocrotonate (26 mmol, 1.3 eq) in anhydrous tetrahydrofuran (10 mL) was added, over 5 minutes, to a suspension of sodium hydride (28 mmol, 1.4 eq, 60% suspension in oil) in anhydrous tetrahydrofuran (15 mL) at 0° C. under nitrogen. The mixture was then stirred at 0° C. for 20 minutes. A solution of the benzaldehyde (20 mmol) in tetrahydrofuran (10 mL) was then added over 10 minutes at 0° C. The mixture was stirred at 0° C. for a further 30 minutes and then it was allowed to stir at room temperature until GC/MS analysis showed that the starting aldehyde had been consumed. The reaction mixture was poured into water, the organic layer was separated and the aqueous layer was extracted with ethyl acetate (×3). The combined organic extracts were then washed with water, then brine, dried (MgSO$_4$) and concentrated in vacuo to give the crude ethyl ester as an oil. The crude products were chromatographed over silica gel. Elution with a mixture of ethyl acetate/hexanes gave the desired ethyl esters as colourless oils.

1.6 General Procedure F—Hydrolysis of Esters

A solution of the ester (10 mmol) in methanol (50 mL) and water (5 mL) was treated with an aqueous solution of 6M potassium hydroxide (20 mmol, 2 eq) and the mixture was heated under reflux until TLC analysis showed that no more starting material was present (usually 2-3 hours). The mixture was then poured into water (50-200 mL) and acidified with concentrated hydrochloric acid to approximately pH 2. The resulting carboxylic acid was collected by filtration, washed with water and dried overnight under high vacuum.

1.7 General Procedure G—Suzuki Reactions of Bromonaphthoic Acids

The bromo-2-naphthoic acid (2 mmol), the appropriate boronic acid (or boronate ester) (2.2 mmol), tetrakis(triphenylphosphine)palladium(0) (0.1 mmol), and solid sodium carbonate (6.8 mmol) were added to the reaction flask which was then purged with nitrogen. Acetonitrile (6 mL) and water (2.5 mL) were added and the mixture was heated under reflux with vigorous stirring until the starting bromo-2-naphthoic acid had been consumed. The reaction mixture was then partitioned between toluene (50 mL) and 0.5M sodium hydroxide solution (100 mL). The aqueous layer was washed with toluene (to remove any triphenylphosphine, 3×20 mL) then acidified to pH 1 with concentrated hydrochloric acid. The naphthoic acid derivatives were extracted into ethyl acetate (4×20 mL). The combined ethyl acetate extracts were washed with water (3×20 mL) and brine (10 mL), then dried (MgSO$_4$), filtered, and concentrated. The residue was analyzed by $^1$H NMR, and chromatographed over silica gel (if required).

1.8 General Procedure H—Preparation of Acylguanidines

To a suspension/solution of carboxylic acid (10 mmol, 1.0 eq) in dichloromethane (30 mL) containing a drop of dimethylformamide was added oxalyl chloride (12 mmol, 1.2 eq) which caused the solution to effervesce. After stirring for 2 h, the resulting solution was evaporated to dryness under reduced pressure. The residue was dissolved in dry tetrahydrofuran (30 mL) and added to a solution of guanidine hydrochloride (0 mmol, 5.0 eq) in 2M aqueous sodium hydroxide (30 mL). The reaction was stirred at room temperature for 1 h and then the tetrahydrofuran layer was separated. The aqueous layer was extracted with chloroform (100 mL) followed by ethyl acetate (100 mL) and the combined organic layers evaporated under reduced pressure. The resulting residue was partitioned between chloroform (200 mL) and 2M aqueous sodium hydroxide (100 mL) and the organic layer was separated and dried (Na$_2$SO$_4$). The solution was filtered and evaporated under reduced pressure to the point where a solid began to precipitate. At this point hexanes were added causing precipitation of the product which was collected by filtration and dried under high vacuum.

2. Specific Experimental Examples of Syntheses

Example 1

4-Hydroxyindan

4-Aminoindan (3.0 g) was added to a solution of concentrated sulphuric acid (2.4 mL) in water (15 mL). More water (15 mL) was added and the mixture cooled to 5° C. A solution of sodium nitrite (1.71 g) in water (4.5 mL) was added portionwise to the mixture while maintaining the temperature below 5° C. After addition was complete the mixture was allowed to warm to room temperature and urea (0.29 g) was added. The mixture was stirred for a further 5 minutes before being heated at 45° C. for 30 minutes. The mixture was then cooled to room temperature and extracted with ethyl acetate. The combined organic extracts were washed with 2M aqueous sodium hydroxide (2×100 mL) and these aqueous extracts were then acidified with hydrochloric acid and extracted with ethyl acetate (3×100 mL). The combined organic extracts were then washed with brine and dried (Na$_2$SO$_4$) before being concentrated in vacuo. The resulting crude product was chromatographed over silica gel. Elution with ethyl acetate/hexanes (1:7) gave 4-hydroxyindan as an orange oil (1.0 g).

Example 2

4-Indanyl triflate

To a solution of 4-hydroxyindan (1.2 g, 8.9 mmol) in pyridine (5 mL) at 0° C. was slowly added trifluoromethanesulphonic anhydride (1.6 mL, 9.5 mmol). The resulting mixture was stirred at 0° C. for 5 minutes before being allowed to warm to room temperature and then stirred for 45 minutes. The mixture was then poured into water and extracted with ethyl acetate (3×25 mL). The combined extracts were washed sequentially with water, 1M aqueous hydrochloric acid, water and brine, then dried ($Na_2SO_4$) and concentrated in vacuo to give the crude triflate as an orange oil (2.13 g, 89%).

Example 3

Methyl 3-(indan-4-yl)acrylate

A mixture of crude 4-indanyl triflate (2.13 g, 8.0 mmol), methyl acrylate (1.01 mL, 11.2 mmol), triethylamine (4.4 mL, 32 mmol, 4 eq) and dichlorobis(triphenylphosphine) palladium (170 mg 0.24 mmol) in dimethylformamide (15 mL) was heated at 85° C. for 71 hours. A small aliquot was removed and worked up for GC/MS analysis which revealed a significant amount of starting material was still present. Additional methyl acrylate (0.7 mL), triethylamine (2 mL) and the palladium catalyst (170 mg) were added and the mixture was heated for a further 24 hours. The mixture was then poured into water, extracted with ethyl acetate, and the organic extracts were washed with water, then brine, dried ($Na_2SO_4$), and concentrated in vacuo to give the crude product as an oil (2.4 g). The crude product was chromatographed over silica gel. Elution with ethyl acetate/hexanes (1:19) gave the starting triflate (812 mg, 38%) as a colourless oil, followed by the desired methyl 3-(indan-4-yl) acrylate as a brown oil (880 mg, 54%).

Example 4

Methyl 3-benzoylcinnamate

To a mixture of 3-bromobenzophenone (5.0 g, 19 mmol), palladium acetate (215 mg, 0.958 mmol), and tri-o-tolylphosphine (290 mg, 0.953 mmol) was added triethylamine (3.3 mL, 45 mmol), toluene (4 mL), and methyl acrylate (2.2 mL, 27 mmol). The mixture was heated at 100° C. for 18 hours at which time TLC analysis showed the reaction was still incomplete. Additional portions of palladium acetate (215 mg, 0.958 mmol), tri-o-tolylphosphine (290 mg, 0.953 mmol), triethylamine (3.3 mL, 45 mmol) and methyl acrylate (2.2 mL, 27 mmol) were added, and the mixture was heated at 110° for a further 18 hours. After cooling to room temperature the mixture was poured into water and extracted with ethyl acetate (3×100 mL). The combined organic extracts were washed sequentially with water and brine, and then dried ($MgSO_4$) and concentrated to a brown oil (5.3 g). The oil was chromatographed over silica gel. Elution with ethyl acetate/hexanes (1:9) afforded methyl 3-benzoylcinnamate (4.6 g, 91%) as a yellow solid.

Example 5

3-Benzoylcinnamic acid

Aqueous 5M potassium hydroxide (10 mL, 50 mmol) was added to a solution of methyl 3-benzoylcinnamate (2.5 g, 9.4 mmol) in methanol (20 mL) and the mixture was stirred at room temperature for 18 hours. The mixture was concentrated and acidified to pH 1 using 1M aqueous hydrochloric acid. The resulting precipitate was collected by filtration and dried under vacuum to give 3-benzoylcinnamic acid (2.2 g, 93%) as a yellow solid.

Example 6

5-(1-Methyl-1H-pyrazol-4-yl)-2-naphthoic acid

A mixture of 5-bromo-2-naphthoic acid (2.12 g, 8.44 mmol), 1-methyl-4-(4,4,5,5-tetramethyl-1,3,2-dioxaborolan-2-yl)-1H-pyrazole (1.84 g, 8.86 mmol), and tetrakis (triphenylphosphine)palladium(0) (502 mg, 0.435 mmol) in a 250 mL round bottomed flask was evacuated and purged with nitrogen (in three cycles). Acetonitrile (40 mL) and 2M aqueous sodium carbonate (10 mL) were added to the mixture via syringe, and the mixture was heated under reflux under nitrogen for 22 hours. The reaction mixture was allowed to cool before the addition of 1M aqueous hydrochloric acid (30 mL) and it was then extracted with ethyl acetate (3×50 mL). The combined organic layers were dried ($MgSO_4$), filtered, and concentrated in vacuo to provide a crude product (2.98 g after air drying). This crude material was dissolved in hot ethanol (150 mL) and filtered while hot to remove a yellow impurity (120 mg). The filtrate was concentrated in vacuo and the residue was recrystallised from dichloromethane (30 mL) to provide 5-(1-methyl-1H-pyrazol-4-yl)-2-naphthoic acid as a white solid (724 mg, 34%). A second crop of 5-(1-methyl-1H-pyrazol-4-yl)-2-naphthoic acid (527 mg, 25%) was obtained from the concentrated mother liquors by recrystallisation from dichloromethane (20 mL).

Example 7

5-(1-Methyl-1H-pyrazol-4-yl)-2-naphthoylguanidine

Oxalyl chloride (1.1 mL, 13 mmol) was added to a solution of 5-(1-methyl-1H-pyrazol-4-yl)-2-naphthoic acid (1.19 g, 4.71 mmol) in anhydrous dichloromethane (200 mL (which was added in portions during the reaction to effect dissolution)) containing dimethylformamide (2 drops) under nitrogen and the mixture was stirred at room temperature for 4.25 hours. The reaction mixture was then heated for 1 hour at 40° C., before being concentrated under reduced pressure. The resulting crude acid chloride was suspended in anhydrous tetrahydrofuran (50 mL) and this mixture was added dropwise to a solution of guanidine hydrochloride (2.09 g, 21.9 mmol) in 2M aqueous sodium hydroxide (15 mL, 30 mmol) and the reaction mixture was then stirred for 30 minutes. The organic phase was separated, and the aqueous phase was extracted with chloroform (3×30 mL) followed by ethyl acetate (3×30 mL). The combined organic extracts were washed sequentially with 1M aqueous sodium hydroxide (60 mL) and water (40 mL), then dried ($Na_2SO_4$) and concentrated in vacuo to give a glassy solid (1.45 g after drying under high vacuum). This solid was dissolved in dichloromethane which was then allowed to evaporate slowly to give 5-(1-methyl-1H-pyrazol-4-yl)-2-naphthoyl-guanidine as a yellow solid (1.15 g, 83%).

Example 8

Ethyl 2,3-methylenedioxycinnamate

Triethyl phosphonoacetate (4.05 mL, 20.2 mmol) was added dropwise to a stirred suspension of sodium hydride (0.80 g, 20 mmol) in anhydrous tetrahydrofuran (20 mL) at 0° C. under nitrogen. The mixture was stirred at 0° C. for 20 minutes. A solution of 2,3-methylenedioxybenzaldehyde (2.50 g, 16 mmol) in tetrahydrofuran (10 mL) was added dropwise at 0° C. The mixture was stirred for 2 hours during which time it was allowed to warm to room temperature. The mixture was poured into water (250 mL), and extracted with ethyl acetate (3×250 mL). The combined organic extracts were then washed with brine, dried ($MgSO_4$) and concentrated in vacuo. The crude product was chromatographed over silica gel. Elution with ethyl acetate/hexanes (1:10) gave ethyl 2,3-methylenedioxycinnamate as a colourless solid (3.50 g, 92%).

Example 9

2,3-Methylenedioxycinnamic acid

A solution of ethyl 2,3-methylenedioxycinnamate (3.40 g) in methanol (25 mL) and water (5 mL) was treated with a solution of potassium hydroxide (4.3 g) in water (25 mL). The mixture was stirred overnight at room temperature before being concentrated in vacuo to half its original volume. The concentrate was then acidified with concentrated HCl to give 2,3-methylenedioxycinnamic acid as a colourless solid (2.81 g, 95%) which was collected by filtration and dried overnight under a vacuum.

Example 10

2,3-Methylenedioxycinnamoylguanidine

Oxalyl chloride (0.68 mL, 7.8 mmol) was added to a suspension of 2,3-methylenedioxycinnamic acid (500 mg, 2.6 mmol) in dichloromethane (5 mL) containing a drop of dimethylformamide. The mixture was stirred for 2.5 hours and the resulting solution was evaporated to dryness under reduced pressure. The residue was dissolved in dry tetrahydrofuran (5 mL) and added to a solution of guanidine hydrochloride (1.24 g, 13 mmol) in 2M aqueous sodium hydroxide (8 mL). The reaction was stirred at room temperature for 1 hour and chloroform was then added. The resulting precipitate of crude product (100 mg) was collected by filtration. The filtrate was extracted with chloroform (3×30 mL) and ethyl acetate (20 mL). The combined organic extracts were washed with 2M aqueous sodium hydroxide (20 mL), water (20 mL), dried ($Na_2SO_4$) and concentrated under reduced pressure to give a further quantity of crude product (400 mg). The two crops of crude product were combined, suspended in chloroform (10 mL) and stirred vigorously for 20 minutes. The resulting 2,3-methylenedioxycinnamoylguanidine (420 mg) was collected by filtration and dried under vacuum.

Example 11

Viral Inhibition Assays

As indicated earlier, methods used to screen for anti-viral activity of the compounds of the present invention have been described in detail in PCT/AU2004/000866, incorporated in its entirety herein by reference.

The inhibition specifically of HIV-1 growth by the compounds of the invention was tested in primary macrophages in vitro using a method similar to that used to assess antibody neutralization (VanCott T C et al (1999)). In the present case, the laboratory adapted HIV-1 strain Ba-L was used, which is known to infect macrophages.

11.1 Macrophage Preparation

Peripheral Blood Mononuclear Cells (PBMC) were prepared from healthy donors using buffy-coat packs obtained from the Australian Red Cross Blood Service (ARCBS). Blood was received the day following donation, and had been depleted of serum and platelets, leaving a small volume (less than 100 mL) of concentrated leukocytes.

Leukocytes were separated from blood cells and granulocytes by density gradient centrifugation (Ficoll Paque) and washed extensively in $PBS^-$ (without Ca/Mg) to remove platelets. Recovered cells were allowed to adhere to plastic tissue culture flasks (Becton Dickinson) for 2 hr, 37° C., 5% $CO_2$, in media (DMEM (high)/10% AB serum/50 ug/mL gentamicin/2 mM L-glutamine) during which time the myeloid cells formed an adherent monolayer leaving lymphocytes unattached.

Non-adherent lymphocytes were removed by washing with warm $PBS^+$ (with Ca/Mg) and were generally discarded. In some cases those cells were recovered and frozen in media/10% DMSO for use in viral stock infections. The adherent monocytes were recovered by scraping gently with a plastic cell scraper. The myeloid cells were then plated into 96-well plates at a cell concentration of $1.5 \times 10^6$/mL, and allowed to fully differentiate over a period of 14 days.

11.2 Assay Protocol

Macrophages were allowed to differentiate over a 14 day period, with media changes as required. On day 14, cells were infected in the presence of decreasing concentrations of BIT compounds over a range 0-10 µM. Samples of 25 µL culture supernatants were removed from each well on day 7 and fresh media plus compound dilution was added.

11.3 Analysis of Viral Inhibition

After 7 days the samples with and without compound were analysed to assess the level of virus present in the wells, using a p24 ELISA (Innotest). Virus levels in samples were converted to "percentage of control virus growth" values based on the controls (containing no compound). From that dose response curve (example FIG. 1) the $IC_{50}$ was calculated and used as a measure of compound anti-HIV activity.

11.4 Cytotoxicity

The toxicity of test compounds to cells in the viral inhibition assay was determined using the MTT assay (Pauwels R, et al. (1988); D'Cruz O J et al. (1999); Joo H. (2003)). This method utilises Thiazolyl Blue (MTT), which is added to the cell culture (100 ug/well), and incubated for 4-5 hours whilst the live, metabolically active cells convert the chemical to its purple coloured metabolite, which forms intracellular crystals. The purple colour is measured colourimetrically (570-590 nm) once cells have been permeabilised using acidified isopropanol containing 10% triton X-100. The most intense colour development occurs in wells where the metabolising cells are most numerous.

The measured OD values were converted to "percentage viability" figures based on the controls (containing no compounds) and the value at which 50% cell viability ($TC_{50}$) was measured could then be estimated. Those values were estimated manually from the Percentage Viability vs Concentration dose response curves (FIG. 1).

11.5 Results

Figure 2:
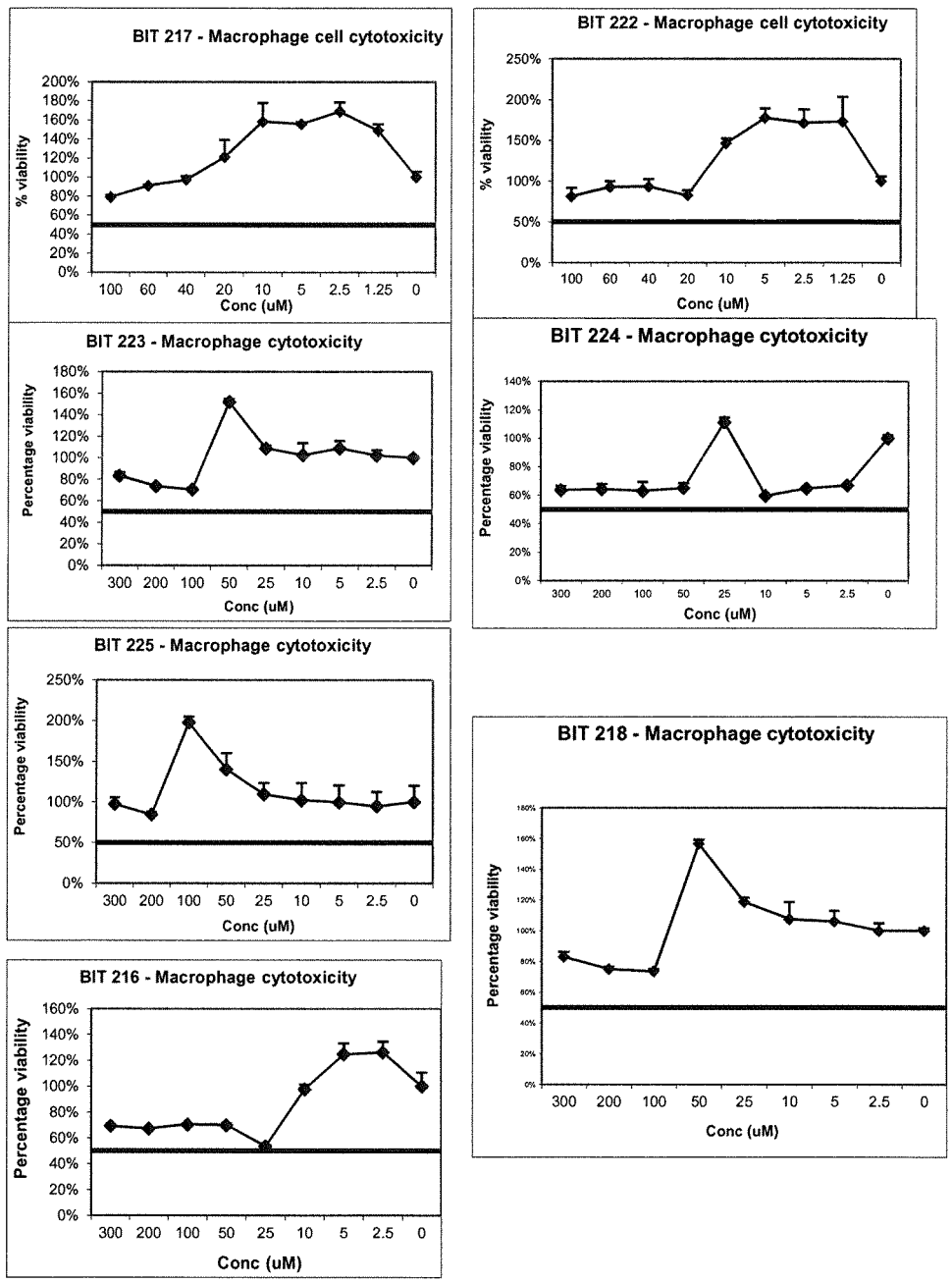
FIG. 2, Cell Cytotoxicity. The compounds were tested for cytotoxicity at a wide range of concentrations.

The $IC_{50}$ values for each compound were calculated from the individual experiments performed and shown in FIGS. 1 and 2.

The compound toxicity to cells in culture was taken into account in inhibition experiments and in separate experiments involving increased concentrations of compound. The Antiviral Index (AI) value was calculated using the formula:

$$AI = \frac{TC_{50}}{IC_{50}}$$

TABLE 1

IC$_{50}$, TC$_{50}$ and AI values for test compounds against HIV-1$_{Ba-L}$ in primary macrophages.

| Compound No. | IC$_{50}$ (μM) | TC$_{50}$ (μM) | AI |
|---|---|---|---|
| (3-benzoyl)cinnamoylguanidine | 0.9 | 25-495 | 28-550 |
| 2,3-methylenedioxycinnamoyl guanidine | 1.1 | >100 | >91 |
| 5-methyl-2-napthoylguanidine | 1.56 | >300 | >192 |
| 3(indan-4-yl)-propenoylguanidine | >10 | >100 | >10 |
| 5-bromo-6-methoxy-2-napthoylguanidine | 0.3 | >300 | >1000 |
| 5-thiophen-3-yl-2-naphthoylguanidine | 1.0 | >200 | >100 |
| 5-(1-methylpyrazol-4-yl)2-naphthoyl-guanidine | 2.5 | >200 | >80 |

All IC$_{50}$ values were estimated from the dose response curves shown in FIG. 1. TC$_{50}$ values were estimated in separate experiments (not shown) where concentrations of compound were greater.

Additional compounds were tested using the same assay system and dose response curves as described above, and their IC$_{50}$ was estimated. Table 2 shows a summary of the data obtained.

TABLE 2

Estimated IC$_{50}$ values for additional compounds of the invention

| Compound No. | IC$_{50}$ (μM) | TC$_{50}$ (μM) |
|---|---|---|
| (1-methoxy-2-napthoyl)guanidine | <2.5 | >50 |
| (3-methoxy-2-napthoyl)guanidine | <2.5 | >50 |
| (5-bromo-2-napthoyl)guanidine | <2.5 | 10-50 |
| (1,4-dimethoxy--2-napthoyl)guanidine | <10 | 10-50 |
| (6-(3-thienyl)-2-napthoyl)guanidine | <0.63 | <10 |
| (6-methyl-2-napthoyl)guanidine | <10 | 10-50 |
| (5-phenyl-2-napthoyl)guanidine | <0.63 | 10-50 |
| (5-(thien-2-yl)-2-napthoyl)guanidine | <0.63 | 10-50 |
| (5-(1,3,5-trimethylpyrazol-4-yl)-2-napthoyl)guanidine | >10 | >50 |
| (5-(1-isobutyl-1H-pyrazol-4-yl)-2-napthoyl)guanidine | <2.5 | 10-50 |
| (5-(3-furyl)-2-napthoyl)guanidine | <0.63 | 10-50 |
| (5-cyclopropyl-2-napthoyl)guanidine | <0.63 | 10-50 |
| (5-chloro-2-napthoyl)guanidine | <2.5 | 10-50 |

Example 12

Anti-Viral Activity of Compounds Using the Bacterial Bioassay Method

The bacterial bioassay method used in the present example to test the anti-viral activity of the compounds against different viral targets was described in detail in PCT/2004/000866, incorporated in its entirety herein by reference. The results of the bacterial bioassay tests are summarised in Table 3 below. Vpu, p7 and M referred to in the table are small membrane proteins encoded by HIV, HCV and Dengue viruses, respectively, which have functional activities supporting viral growth and/or replication.

Although the invention has been described with reference to specific embodiments it will be understood that variations and modifications in keeping with the principles and spirit of the invention described are also encompassed.

TABLE 2

Mean Bacterial Bioassay Assay Scores For Compounds Of The Invention

| Compound Name | BIT# | Average Bacterial Assay Score | | |
|---|---|---|---|---|
| | | Vpu | HCV p7 | Den M |
| (3-benzoyl)cinnamoylguanidine | 216 | 1.3 | 1.3 | 1.5 |
| 2,3-methylenedioxycinnamoyl guanidine | 217 | 1.8 | 1.0 | |
| 5-methyl-2-napthoylguanidine | 218 | 1.8 | 1.7 | 1.3 |
| 3(indan-4-yl)-propenoylguanidine | 222 | 1.2 | 2.0 | 2.2 |
| 5-bromo-6-methoxy-2-napthoylguanidine | 223 | 0 | 0.0 | |
| 5-thiophen-3-yl-2-naphthoylguanidine | 224 | 2.2 | 1.1 | 1.3 |
| 5-(1-methylpyrazol-4-yl)2-naphthoylguanidine | 225 | 1.4 | 1.2 | 0.9 |
| 3,4-dichlorocinnamoyl guanidine | 300 | 1.52 | 0.67 | 3.40 |
| (1-methoxy-2-napthoyl)guanidine | 301 | 1.54 | 0.25 | 0.50 |
| (3-methoxy-2-napthoyl)guanidine | 302 | 1.04 | 0.42 | 0.50 |
| (5-bromo-2-napthoyl)guanidine | 303 | 0.22 | 0.00 | 2.10 |
| (1,4-dimethoxy-2-napthoyl)guanidine | 304 | 0.62 | 0.33 | 1.90 |
| (6-(3-thienyl)-2-napthoyl)guanidine | 305 | 0.38 | 0.00 | 1.15 |
| (6-methyl-2-napthoyl)guanidine | 306 | 0.52 | 0.25 | 2.53 |
| (5-phenyl-2-napthoyl)guanidine | 307 | 0.12 | 0.08 | 2.40 |
| (5-thien-2-yl)-2-napthoyl)guanidine | 308 | 0.45 | 0.08 | 2.40 |
| (5-(1,3,5-trimethylpyrazol-4-yl)-2-napthoyl)guanidine | 309 | 0.12 | 0.00 | 0.00 |
| (5-(1-isobutyl-1H-pyrazol-4-yl)-2-napthoyl)guanidine | 310 | 0.00 | 0.00 | 1.60 |
| (5-(3-furyl)-2-napthoyl)guanidine | 311 | 0.42 | 0.42 | 1.60 |
| (5-cyclopropyl-2-napthoyl)guanidine | 312 | 0.50 | 0.80 | 2.25 |
| (5-chloro-2-napthoyl)guanidine | 313 | 0.30 | 1.30 | 3.00 |
| (6-(1-methylpryazol-4-yl)-2-napthoyl)guanidinium acetate | 314 | 0.00 | 3.30 | 1.60 |
| (5-(2,6-dimethoxypryridin-3-yl)-2-napthoyl)guanidine | 315 | 0.20 | 0.30 | 1.00 |
| (5-(2-chlorophenyl)-2-napthoyl)guanidine | 316 | 0.20 | 0.80 | 0.50 |
| (5-(4-(acetylamino)phenyl)-2-napthoyl)guanidine | 317 | 0.00 | 0.20 | 0.40 |

TABLE 2-continued

Mean Bacterial Bioassay Assay Scores For Compounds Of The Invention

| Compound Name | BIT# | Average Bacterial Assay Score | | |
|---|---|---|---|---|
| | | Vpu | HCV p7 | Den M |
| (5-(3-(acetylamino)phenyl)-2-napthoyl)guanidine | 318 | 2.00 | 0.30 | 0.35 |
| (5-(4-((methylsulphonyl)amino)phenyl)-2-napthoyl)guanidine | 319 | 0.00 | 0.00 | 0.15 |
| ASSAY POSITIVE CONTROL | | | | |
| (3-Bromocinnamoyl)guanidine | BIT067 | 2.88 | | |
| 5-bromo-2-fluorocinnamoylguanidine | BIT124 | | 2.25 | |
| 5-(2'-bromophenyl)penta-2,4-dienoylguanidine | BIT128 | | | 2.87 |

REFERENCES

VanCott T C, Mascola J R, Loomis-Price L D, Sinangil F, Zitomersky N, McNeil J, Robb M L, Birx D L, Barnett S. (1999) *J. Virol.* 73(6):4640-50

Pauwels R, Balzarini J, Baba M, Snoeck R, Schols D, Herdewijn P, Desmyter J and De Clercq E, (1988) *J. Virolog. Methods.* 20:309-321

D'Cruz O J, Shih M-J, Yiv S H, Chen C-L, Uckun F M. (1999) *Mol. Hum. Reprod.* 5(5):421-432

Joo, Hong-Gu. (2003) *J. Vet. Sci.* 4(3):229-234

The invention claimed is:

1. A compound which is:
(6-(1-methylpyrazol-4-yl)-2-naphthoyl)guanidine
having the structure

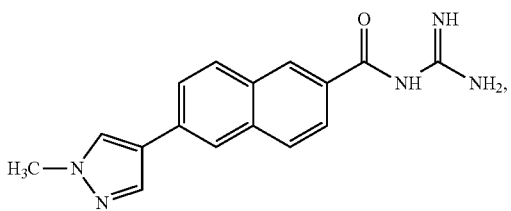 [SMILES: Cn1cc(-c2ccc3cc(C(=O)NC(=N)N)ccc3c2)cn1]

or a pharmaceutically acceptable salt thereof.

2. The compound of claim 1, wherein the compound has anti-viral activity.

3. The compound of claim 2, wherein the compound is capable of reducing, retarding or otherwise inhibiting viral growth and/or replication.

4. The compound of claim 2, wherein the antiviral activity is directed against viruses of the Flavivirus or Lentivirus families.

5. The compound of claim 4, wherein the virus is selected from the group consisting of Hepatitis C virus (HCV), Human Immunodeficiency Virus (HIV), and Dengue virus.

6. The compound of claim 4, wherein the virus is selected from the group consisting of HCV, HIV-1, HIV-2 and Dengue virus.

7. A pharmaceutical composition comprising a compound according to claim 1, optionally in combination with one or more pharmaceutical acceptable carriers or adjuvants.

8. The pharmaceutical composition of claim 7, further comprising one or more known antiviral agents.

9. A method for reducing, retarding or otherwise inhibiting growth and/or replication of a virus comprising contacting a cell infected with said virus or exposed to said virus with a compound according to claim 1, wherein the virus is selected from the Lentivirus and Flavivirus families.

10. A method for the treatment of a subject exposed to or infected by a virus comprising the administration to said subject of a compound according to claim 1, wherein the virus is selected from the Lentivirus and Flavivirus families.

11. A method for the treatment of a subject exposed to or infected by a virus comprising the administration to said subject of a compound according to claim 1, in conjunction with another one or more known antiviral agents, wherein the virus is selected from the Lentivirus and Flavivirus families.

12. The method according to claim 10, wherein the virus is selected from the group consisting of Hepatitis C virus (HCV), Human Immunodeficiency Virus (HIV), and Dengue virus.

13. A method according to claim 12, wherein the virus is selected from the group consisting of HCV, HIV-1, HIV-2 and Dengue virus.

14. The method according to claim 10, wherein the subject undergoing treatment is a mammal selected from the group consisting of human, primate, livestock animal, companion animal, laboratory test animal or captive wild animal.

* * * * *